United States Patent
Sakai et al.

(10) Patent No.: US 8,995,748 B2
(45) Date of Patent: Mar. 31, 2015

(54) DEFECT IMAGE PROCESSING APPARATUS, DEFECT IMAGE PROCESSING METHOD, SEMICONDUCTOR DEFECT CLASSIFYING APPARATUS, AND SEMICONDUCTOR DEFECT CLASSIFYING METHOD

(75) Inventors: Tsunehiro Sakai, Mito (JP); Shigeki Kurihara, Hitachinaka (JP); Yutaka Tandai, Hitachinaka (JP); Tamao Ishikawa, Hitachinaka (JP); Yuichi Hamamura, Yokohama (JP); Tomohiro Funakoshi, Hitachinaka (JP); Seiji Isogai, Hitachinaka (JP); Katsuhiko Ichinose, Tokorozawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 648 days.

(21) Appl. No.: 13/375,880

(22) PCT Filed: Jun. 1, 2010

(86) PCT No.: PCT/JP2010/059237
§ 371 (c)(1),
(2), (4) Date: Feb. 22, 2012

(87) PCT Pub. No.: WO2010/140577
PCT Pub. Date: Dec. 9, 2010

(65) Prior Publication Data
US 2012/0141011 A1 Jun. 7, 2012

(30) Foreign Application Priority Data
Jun. 2, 2009 (JP) .................................. 2009-132888

(51) Int. Cl.
*G06T 7/00* (2006.01)
*G01N 21/95* (2006.01)
*H01L 21/66* (2006.01)

(52) U.S. Cl.
CPC ............... *G06T 7/001* (2013.01); *G06T 7/0024* (2013.01);
(Continued)

(58) Field of Classification Search
None
See application file for complete search history.

(56) References Cited

U.S. PATENT DOCUMENTS

2006/0065645 A1* 3/2006 Nakasu et al. ............ 219/121.68
2009/0074286 A1 3/2009 Kitazawa et al.
2009/0136121 A1* 5/2009 Nakagaki et al. ............. 382/149
(Continued)

FOREIGN PATENT DOCUMENTS

| JP | 2005-283326 | 10/2005 |
|---|---|---|
| JP | 2009-010286 | 1/2009 |
| JP | 2009-071136 | 4/2009 |

OTHER PUBLICATIONS

International Search Report for International Application No. PCT/JP2010/059237 mailed Aug. 31, 2010.

*Primary Examiner* — Randolph I Chu
*Assistant Examiner* — Nathan Bloom
(74) *Attorney, Agent, or Firm* — Brundidge & Stanger, P.C.

(57) ABSTRACT

A defect image processing apparatus uses a normalized cross correlation to image-match a layout image (52) acquired from a design data with an image acquired by removing, from a defect image (53), the defect area portions thereof, and displays, as a result of that matching, a layout image and defect image (54) on the display device. In the displayed layout image & defect image (54), not only the layout image, the layer of which is the same as that of the defect image (53), but also a layout image of another layer is displayed superimposed on the defect image (53). This makes it easier to analyze the factor of a systematic defect having occurred due to a positional relationship with another layer.

13 Claims, 8 Drawing Sheets

(52) U.S. Cl.
CPC . *G01N 21/9501* (2013.01); *G06T 2207/30148* (2013.01); *H01L 22/12* (2013.01); *H01L 22/20* (2013.01); *G06T 2200/24* (2013.01); *G06T 2207/10056* (2013.01)

USPC .......................................................... 382/149

(56) References Cited

U.S. PATENT DOCUMENTS

2010/0067779 A1* 3/2010 Reich et al. .................... 382/145
2011/0286656 A1* 11/2011 Kulkarni et al. ............... 382/144

* cited by examiner

```
[INFORMATION]
~Skipped~
Image magnification(low)=8000
Image magnification(high)=15000
Image resolution(low)=512
Image resolution(high)=512
    .
    .

[RESULT]
Center of mass coordinate of defect portion: X=230.000
Center of mass coordinate of defect portion: Y=235.500
```
—20

DEFECT IMAGE PROCESSING APPARATUS, DEFECT IMAGE PROCESSING METHOD, SEMICONDUCTOR DEFECT CLASSIFYING APPARATUS, AND SEMICONDUCTOR DEFECT CLASSIFYING METHOD

FIELD OF THE INVENTION

The present invention relates to an image processing technology and a semiconductor defect classifying technology using the image processing technology for a defect image, which is acquired by an inspection device, of a defect on a wafer or chip generated during a fabrication process of a semiconductor device.

DESCRIPTION OF THE RELATED ART

Recently, various kinds of semiconductor defect inspection device such as, a dark field (DF) defect inspection device, a bright field (BF) inspection device and an electron beam (EB) defect inspection device have been developed, and defect inspection methods using these devices have been also progressed in accordance with a progress of fine pattering. For example, based on positional information of a defect detected by these defect inspection devices, a clear image of the defect is acquired by a review device, and ADC (Automatic Defect Classification) is conducted using the acquired image in order to automatically classify the defect into a defect category.

So far, an origin of fabrication yield lowering of a semiconductor device has been mainly a defect which is randomly generated, such as foreign materials and impurities. Then, the yield has been maintained by studying the origin of the defect using a defect inspection device and a defect review device and taking countermeasures for the fabrication process. However, a minimum line width of pattern of a semiconductor device in recent years is already less than 65 nm, and the fine pattering is further progressing to 45 nm, 32 nm. In accordance with this progress, a ratio of the defect that is generated depending on a design layout is increasing, instead of the random defect.

This kind of defect that depends on a design layout is called a systematic defect, and a large amount of defective product may be fabricated at the initial stage of mass production of the product in some cases. For example, a wiring having a specific shape may be narrowed by the effect of patterns of neighboring wirings, or may be easily short-circuited with an adjacent wiring. In addition, an etching shortage of oxide film at a contact hole may be caused depending on a shape of impurity diffused layer below the oxide film, and as a result, a wiring layer of the upper layer and the diffused layer of the lower layer are not electrically connected, in some cases. Therefore, in order to take countermeasures for the systematic defect, it is required to analyze the origin and examine both the design data and fabrication process conditions.

In order to examine/analyze the origin of the systematic defect, it is required to analyze a relationship between a defect position and a layout pattern of design data. For example, Patent Document 1 discloses a method that correlates a review image containing a defect with a layout pattern in order to analyze an origin of the defect, and determines that the defect is a systematic defect based on, for example, information of defect density in the area to which a position of the defect belongs.

PRIOR ART DOCUMENT

Patent Document

[Patent Document 1] Japanese Patent Publication No. 2009-10286

SUMMARY OF THE INVENTION

Problems to be Solved by the Invention

In order to analyze a positional relationship between a defect position and a layout pattern, it is required to accurately and efficiently correlate a review image with a layout pattern. Patent Document 1 describes a method for correlating the review image with the layout pattern by focusing on a characteristic shape of a periphery portion of a semiconductor device chip. However, there is no specific description on a matching method of an image in the review image of large magnification.

It is, therefore, an object of the present invention to provide a defect image processing apparatus, a defect image processing method, a semiconductor defect classifying apparatus and a semiconductor defect classifying method that are capable of highly-accurate and efficient image matching between a review image (hereinafter, referred to as defect image) containing a defect and a layout pattern (hereinafter, referred to as layout image) based on design data.

Means for Solving the Problems

In order to achieve the foregoing object, according to the present invention, there is provided a defect image processing apparatus, which includes: a matching processing unit that executes an image matching between a defect image which is acquired by a defect inspection device or a defect review device of a semiconductor device and contains a defect of the semiconductor device and a layout image which is generated from a layout data of the semiconductor device and corresponds to an area of the defect image of a layer identical to the layer containing the defect; and an output processing unit that displays a superimposed image which is formed by superimposing the defect image on the layout image on a display unit, the defect image being matched with the layout image by the matching processing unit. when the image matching between the defect image and the layout image is executed, the matching processing unit removes an image of an area of a defect portion from the defect image and executes the image matching between the layout image and the defect image that is formed by removing the image of the area of the defect portion from the defect image.

In the present invention, when the image matching between the defect image and the layout image is executed, the image matching is executed after a defect image portion of the defect image is removed. Therefore, a failure of the image matching is reduced even if the defect exists in the defect image of large magnification, and as a result, a failure probability of the image matching decreases and efficiency of the image matching can be improved.

Effects of the Invention

Efficiency of matching processing between a defect image acquired by, for example, a defect review device and a layout image based on design data can be improved.

EMBODIMENT FOR EMBODYING THE INVENTION

Hereinafter, an explanation will be given in detail of a preferred embodiment of a defect image processing apparatus and a defect image processing method according to the present invention by referring to drawings. Meanwhile, in the explanation below and attached drawings, a constituent having substantially an identical function is given the same reference, and the duplicate explanation will be omitted.

Figure 1:
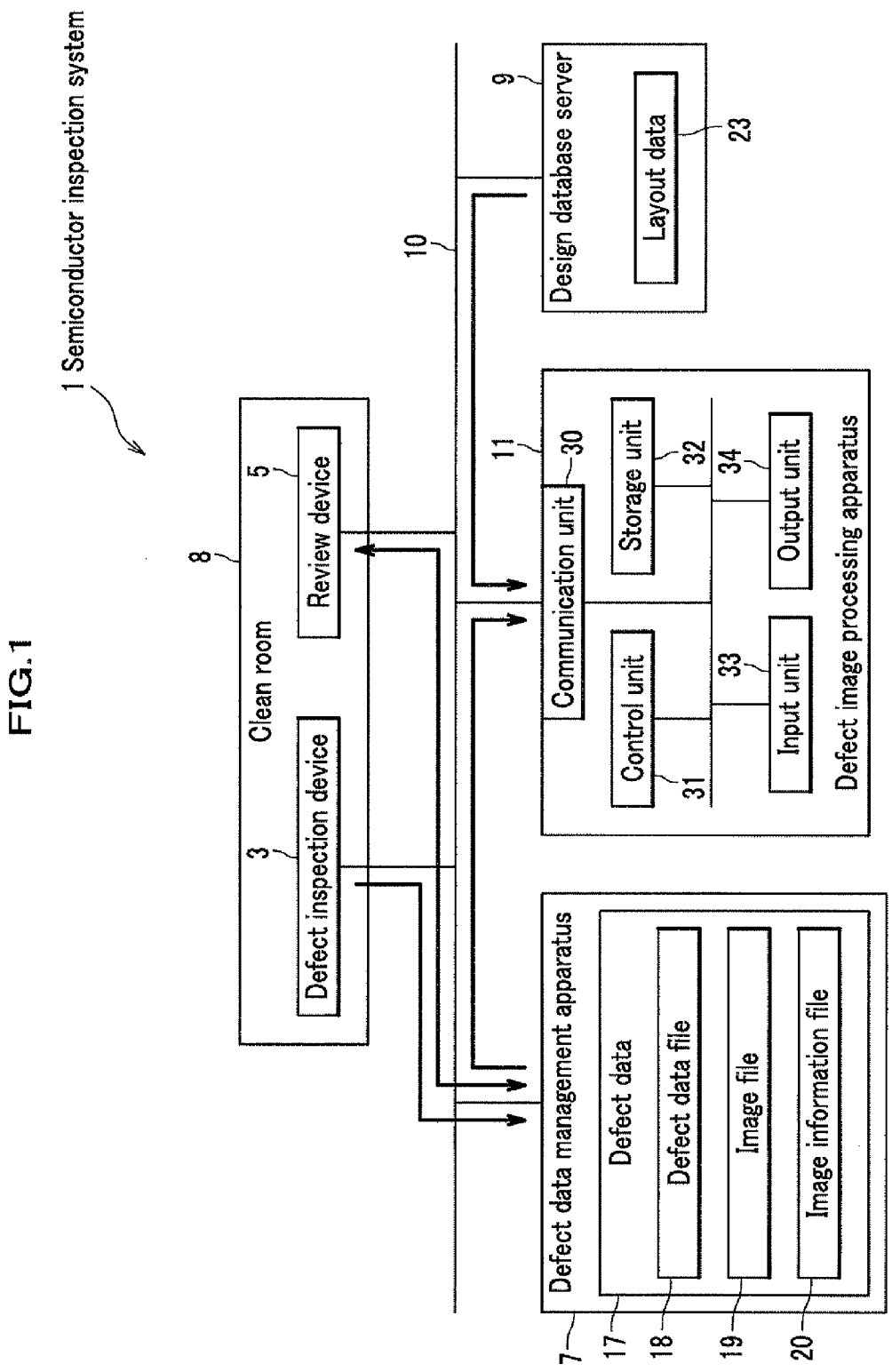
FIG. 1 is an illustration showing one example of a configuration of a semiconductor inspection system including a defect image processing apparatus according to an embodiment of the present invention.

FIG. 1 is an illustration showing one example of a configuration of a semiconductor inspection system including a defect image processing apparatus according to an embodiment of the present invention. As shown in FIG. 1, the semiconductor inspection system 1 includes, for example, a defect inspection device 3, a review device 5, a defect data management apparatus 7, a design database server 9 and a defect image processing apparatus 11. The defect inspection device 3, the review device 5, the defect data management apparatus 7, the design database server 9 and the defect image processing apparatus 11 are connected to each other so as to enable data transmission and reception via a network 10.

A semiconductor fabrication process consists of various kinds of processes (not shown), such as, impurity doping, film formation and etching, and the semiconductor fabrication process is built inside a clean room 8 maintaining a clean environment due to a necessity of microfabrication. The defect inspection device 3 and the review device 5 that inspect a status of defects of a semiconductor wafer processed in respective fabrication processes are installed inside the clean room 8.

The defect inspection device 3 is, for example, a dark filed defect inspection device, a bright field defect inspection device and an electron beam defect inspection device that detects a defect of a semiconductor wafer under fabrication, and detects a defect generated on a surface of an inspection target device. In addition, the defect inspection device 3 has a function to acquire an observation image (referred to as review image or defect image) of the detected defect.

The review device 5 is, for example, a scanning electron microscope (SEM: Scanning Electron Microscope), and based on coordinate information of a defect detected by the defect inspection device 3 on the semiconductor wafer, acquires a detailed review image of the defect. The review device 5 also has an ADC function for classifying a category of a defect origin of the detected defect.

The defect data management apparatus 7 receives various kinds of data of defects of a semiconductor wafer, which are acquired and transmitted by the defect inspection device 3 or the review device 5, through the network 10, and stores and manages the data as a defect data 17. Here, for example, a defect data file 18, an image file 19 and an image information file 20 are included in the defect data 17.

The defect data file 18 is a file that stores defect data, such as a defect identification number for identifying a defect detected by the defect inspection device 3, a defect position coordinate of the defect expressed by a coordinate on a die to be determined against a predetermined reference point (origin) set in each die (chip), a defect size and a category of a defect origin.

The image file 19 is a file that stores data of a defect image (review image) acquired by the defect inspection device 3 or the review device 5 which are provided with a reviewing function.

Figures 2, 3:
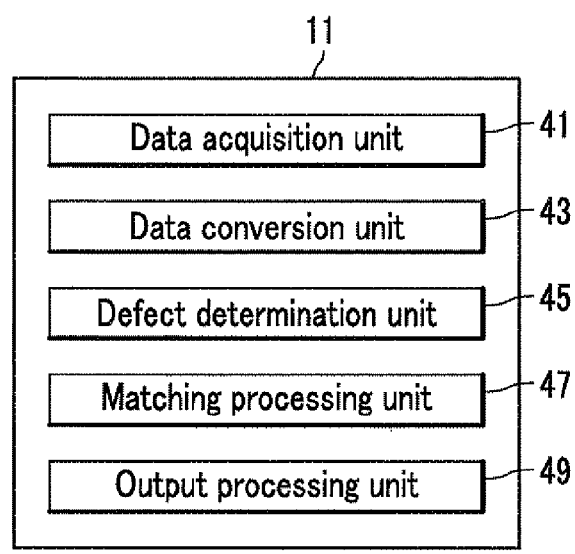
FIG. 2 an illustration showing one example of data stored in an image information file used in a defect image processing apparatus.
FIG. 3 is an illustration of one example of a function block configuration of a defect image processing apparatus according to the embodiment of the present invention.

The image information file 20 is a file for storing information which is prepared correlated with each image file 19 and indicates an acquisition status of the each image file 19. As one example is shown in FIG. 2, the image information file 20 consists of several pieces of information, such as an image magnification (low magnification, high magnification) of a defect image included in the image file 19, an image resolution (low resolution, high resolution), a defect area coordinate containing a defect, a center of mass coordinate of the defect area and the number of frame images that form the image by being superimposed.

Here, the image magnification of a defect image is a magnification of the defect image when the defect image is acquired by the defect inspection device 3 or the review device 5. The magnification of the defect image is generally determined based on, for example, a minimum dimension of a pattern defined by a design rule of a semiconductor device, a size of a defect (defect size) which affects on the fabrication yield of the semiconductor device, or a magnification capable of including the defect in the viewing field (FOV: Field Of View).

The design database server 9 stores and manages the layout data 23 of a semiconductor device (for example, integrated circuit chip) for each semiconductor device which is fabricated on a semiconductor wafer through a predetermined semiconductor fabrication process. The layout data 23 is a design data relating to a physical arrangement of, for example, elements and wirings that form the semiconductor device, and the layout data 23 is also a data defining a shape of a mask (mask pattern) to be used in each fabrication process.

The defect image processing apparatus 11 acquires a defect image of an inspection target semiconductor wafer from the defect data management apparatus 7 and a layout image of elements and wirings to be formed on a semiconductor wafer from the design database server 9, and compares both images and provides the result of the comparison to a defect analyzing processing to be conducted later.

The defect image processing apparatus 11 consists of a computer such as a workstation and a personnel computer, and includes a communication unit 30, a control unit 31, a storage unit 32, an input unit 33 and an output unit 34.

The control unit 31 consists of, for example, a central processing unit (CPU) or a microprocessor. The control unit 31 controls the other respective units and executes a matching processing, described later. The storage unit 32 consists of a storage device, for example, a volatile memory such as a random access memory (RAM), a non-volatile memory such as a flush memory and a hard disc, and stores programs for executing the matching processing, described later, and a defect image as well as a layout data transmitted from the defect data management apparatus 7 and the design database server 9, respectively.

The communication unit 30 transmits and receives data to and from the defect inspection device 3, the review device 5, the defect data management apparatus 7 and the design database server 9 via the network 10. That is, based on instruction by the control unit 31, the communication unit 30 acquires, for example, the defect data file 18 relating to defect data of an inspection target semiconductor wafer, the image file 19 and the image information file 20 from the defect data management apparatus 7, and also acquires the layout data 23 of an integrated circuit chip to be formed on the semiconductor wafer from the design database server 9.

The input unit 33 consists of input tools such as a keyboard, a mouse and various kinds of buttons, and the output unit 34 consists of output tools such as a liquid crystal display (LCD) and a printer.

FIG. 3 is an illustration of one example of a function block configuration of a defect image processing apparatus 11 according to the embodiment of the present invention. As shown in FIG. 3, the defect image processing apparatus 11 includes a data acquisition unit 41, a data conversion unit 43, a defect determination unit 45, a matching processing unit 47 and an output processing unit 49.

The data acquisition unit 41 acquires the defect data 17 from the defect data management apparatus 7 and the layout data 23 from the design database server 9 through the network 10. The data conversion unit 43 converts the defect data 17 acquired from the defect data management apparatus 7 and the layout data 23 acquired from the design database server 9 into a data format which can be used in the defect determination unit 45 and in the matching processing unit 47, which will be described later.

The defect determination unit 45 determines whether the defect is a random defect or a systematic defect based on the acquired defect data 17. Here, the random defect is a defect to be generated caused by dusts and foreign materials. The matching processing unit 47 matches the origin and magnification of the defect image included in the defect data 17 with those of the layout data so that the respective coordinate axes match to each other, and execute image matching. The output processing unit 49 outputs, for example, a defect image converted by the data conversion unit 43, a layout image based on the layout data 23, a result of matching processing by the matching processing unit 47, a defect position and a result of category classification, to the output unit 34.

Meanwhile, a function of each function block is realized as follows. Namely, the control unit 31 reads out and executes a predetermined processing program stored in advance in the storage unit 32 in order to realize the function.

Figure 4:
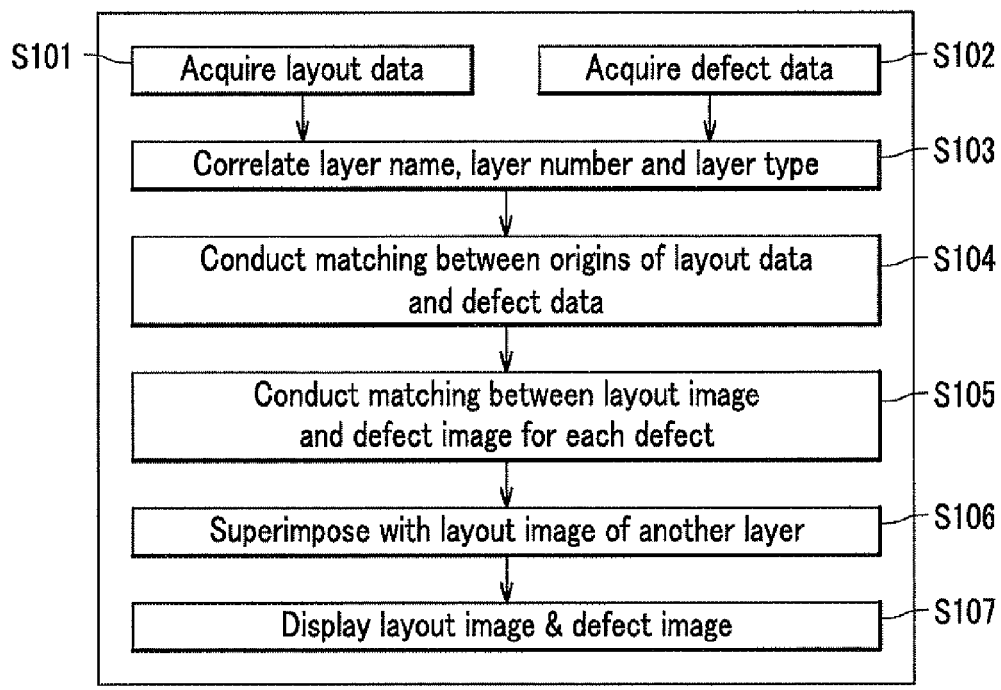
FIG. 4 is a flowchart showing one example of a procedure of a matching processing between a defect image and a layout image in a defect image processing apparatus according to the embodiment of the present invention.

Next, an explanation will be given of operations of the defect image processing apparatus 11 in reference to drawings following FIG. 4. FIG. 4 is a flowchart showing one example of a procedure of a matching processing between a defect image and a layout image.

In FIG. 4, the data acquisition unit 41 first acquires the layout data 23 from the design data base server 9 via the network 10 (step S101) and the defect data 17 from the defect data management apparatus 7 (step S102). The acquired layout data 23 and defect data 17 are converted by the data conversion unit 43 into a data format that can be read out by the matching processing unit 47.

Next, the matching processing unit 47 correlates an inspection target layer in the fabrication process including a defect with a single layer or a plurality of layers that are targets of the image matching in the layout data 23 as a matching target layer. Namely, the matching processing unit 47 correlates the inspection target layer in the fabrication process with a layer name, a layer number and a layer type of a layer to be matched in the layout data 23 (step S103).

In the processing of the correlation, an input processing from the input unit 33 by the operator and a reading processing of recipe data which is set in advance maybe included therein, however, the details will be omitted.

It is noted that the operator can handle a matching target layer in the layout data 23 by the name of the inspection target in the fabrication process by executing the foregoing correlation. In addition, at the time, for example, a defect origin analysis may be conducted using a displayed image without concerning about the layer number and the layer type.

Next, the matching processing unit 47 matches an origin of the layout data 23 with the origin of the defect data 17 (step S104). For example, in the layout data 23, the origin of coordinate system of data indicating a position may be set at the center of a die (chip) in some cases. On the other hand, in the defect data 17, the origin of coordinate system of data indicating a position may be set at the bottom-left corner of the die (chip) in some cases. In this case, the matching processing unit 47 matches the origin and coordinate axes of the layout data 23 with those of the defect data 17 so that the same positional information may be expressed by the same data in both the layout data 23 and the defect data 17.

Meanwhile, if the origin of the layout data 23 is matched with the origin of the defect data 17 using the layout data 23 of a single layer, a matching of the origin of the layout data 23 with that of another layer is unnecessary.

Next, the matching processing unit 47 matches a layout image of a matching target layer acquired from the layout data 23 corresponding to a position of the defect with a defect image stored in the image file 19 for each defect included in the defect data 17 (step S105). In this case, since the matching of the origin was already completed in the previous step S104, a layout image corresponding to a coordinate position can be easily acquired from the coordinate position of the defect. However, data of the coordinate position contains errors generated at the detection of the defect, and there may be a little gap of the position between the layout image and the defect image in many cases. Therefore, a pattern matching between the layout image and the defect image is conducted using an area wider than the viewing field of the defect image.

Meanwhile, although not shown, the matching processing unit 47 executes a magnification matching of an image prior to the image matching. At this time, a magnification of the defect image is the magnification at the acquisition of the defect image by the defect inspection device 3 or the review device 5, and is stored in the image information file 20 (see FIG. 2). Then, the matching processing unit 47 refers to the magnification of the defect data 17 stored in the image information file 20 and calculates a magnification for superimposing the defect image on the layout image acquired from the layout data 23, and as a result, both the images can be matched under the same coordinate system.

In the defect image processing apparatus 11 according to the present embodiment, since the defect image data (image file 19) and the magnification thereof (image information file 20) were correlated with each other and already sent from the defect inspection device 3 or the review device 5 (see FIG. 2), the matching processing unit 47 can generate the layout image having the same magnification with the defect image and execute the image matching without receiving the input of the magnification information from the operator. As a result, it becomes unnecessary for the operator to concern about the magnification of the matching target defect image, thereby resulting in improvement of handling of the defect image processing apparatus 11 for the operator.

Next, the matching processing unit 47 superimposes the defect image on a layout image of an upper layer or a lower layer, that is, another layer of the matching target layer (step S106). Namely, the matching processing unit 47 acquires a layout image of the same area with the defect image in a layer different from the layer containing the defect from the layout data 23, and superimposes the acquired layout image on the defect image.

Next, as a result of the matching processing, the matching processing unit 47 superimposes layout images of the matching target layer and the upper layer or the lower layer, that is, another layer of the matching target layer on the defect image, and displays the superimposed image on the output unit 34 (step S107). It is noted that a plurality of the upper layers and/or the lower layers, that is, other layers may be selected.

As described above, a layout image of another layer which may cause a defect can be selected, can be referred to and can be displayed as appropriate in the upper layer or the lower layer of the layer containing the defect. Therefore, the operator can evaluate existence or non-existence of effects of another layer on the defect. For example, if the inspection target layer is a poly-Si layer, information such as whether or not the lower layer of the defect is an active area (impurity doped area) of n-type or p-type, or whether or not the lower layer is a non-active area, can be acquired, and based on the information, it becomes possible to determine, for example, whether or not the defect corresponds to a systematic defect.

In addition, if there is a layout data of a floor plan of a layer, an evaluation on whether the defect is a systematic defect or not can be performed by a simplified manner. Namely, whether the defect is located in a memory cell area, or in a wiring area, or in a periphery circuit area, or in a dummy pattern area, is determined by comparing a position of the defect with a block area defined by the floor plan, and based on the result, the defect can be determined whether the defect corresponds to a systematic defect or not.

Figure 5:
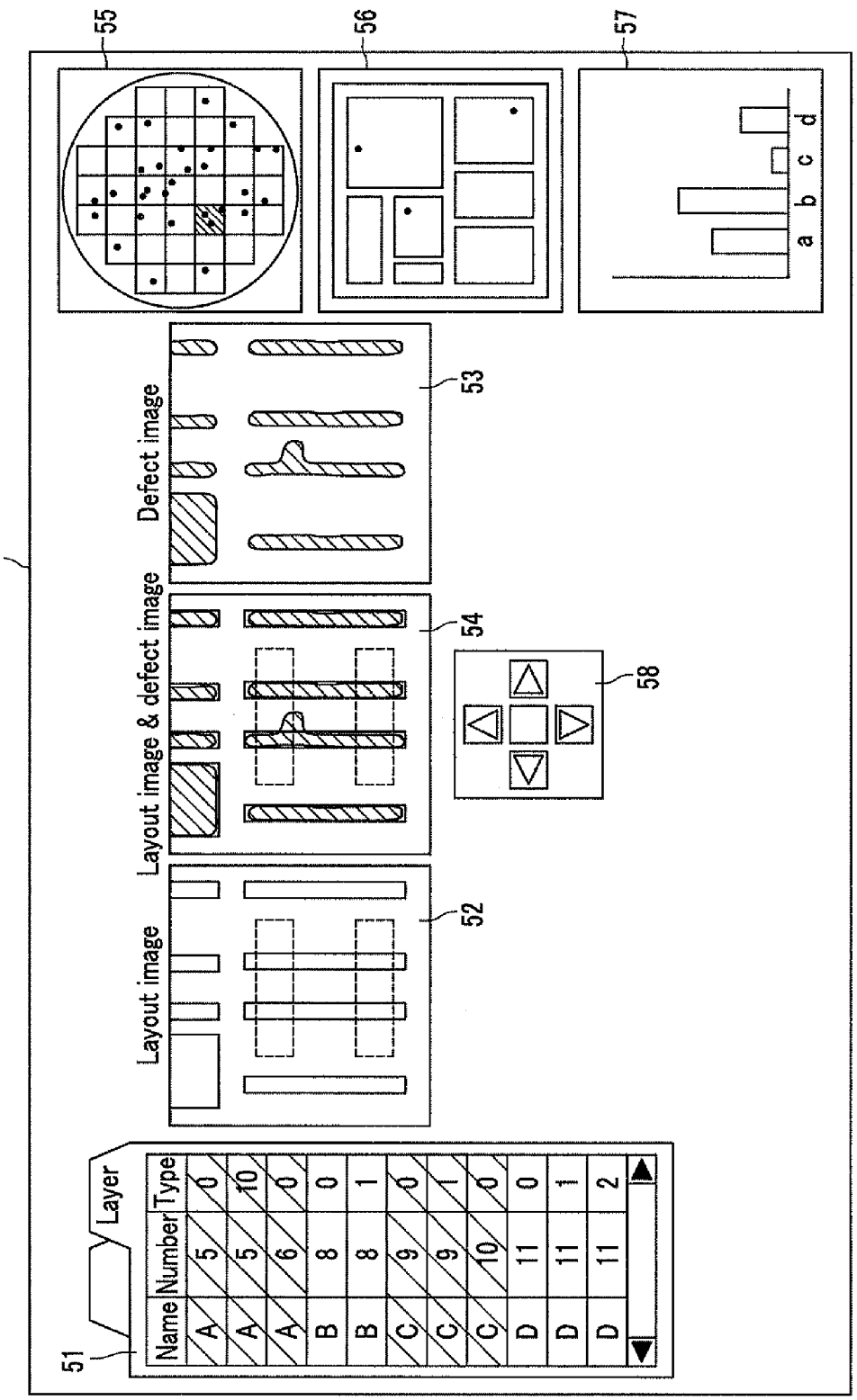
FIG. 5 is an illustration showing one example of a screen display in a defect image processing apparatus according to the embodiment of the present invention.

FIG. 5 is an illustration showing one example of a screen display by the output unit 34. As shown in FIG. 5, for example, a layer correlation display 51, a layout image 52, a defect image 53, a layout image & defect image 54, a wafer map display 55, a die map display 56 and a defect category display 57 are shown on a display screen 50.

The layer correlation display 51 indicates a name, a number and a type of a layer in the layout data 23 correlated in the step S103 with the layer of the fabrication process containing a defect. It is noted that even if a name of the layout is the same, there is a layout having a different number and a different type, because a design or a fabrication process of the layer is different. The operator can select a layer to display on the display screen 50 from the layout data 23 as appropriate, using the layer correlation display 51.

The layout image 52 is an image of, a so-called layout pattern which is generated based on the layout data 23. In FIG. 5, a layout image of a matching target layer (an inspection target layer, which is a layer in the layout data 23 corresponding to a layer containing a defect) is shown by solid lines and a layout image above or below the matching target layer is shown by dotted lines. In addition, the defect image 53 is a review image acquired by, for example, the review device 5, and is displayed using the image file 19 included in the defect data 17.

The layout image & defect image 54 displays a matching result of the layout image 52 and the defect image 53. Namely, the layout image & defect image 54 is the image that is formed by superimposing a result of matching processing on a layout image of another layer which is different from the matching target layer. Meanwhile, a single or plurality of other layers may be selected as appropriate by, for example, input operation of the operator.

The layout image & defect image 54 is displayed even if a matching processing between the layout image and the defect image in the step S105 is failed. In this case, since the layout image is displayed shifted a little from the defect image due to an error of a detection position of the defect image, the layout image may be moved manually and superimposed on the defect image, by clicking a shifting button 58 (up, down, right or left button) using, for example, a mouse.

The wafer map display 55 is a display indicating a position of each defect on the wafer included in the defect data 17 by a position of a dot. In addition, the die map display 56 is a display similarly indicating a position of the defect within a die by a position of a dot. In the die map display 56, since data of the floor plan is superimposed on the die, it is easily understood a block, such as a control circuit unit, an arithmetic circuit unit and a RAM unit within the die, where each defect is located.

In addition, in the display screen 50, if the operator clicks a dot displayed in the wafer map display 55 or the die map display 56 by selecting the dot using, for example, a mouse, the layout image 52, the defect image 53 and the layout image & defect image 54 of the defect corresponding to the selected dot are displayed.

The defect category display 57 is a display indicating a defect distribution by category of defect origin which is classified by ADC of the defect inspection device 3. Namely, in the defect category display 57, a, b, c and d on horizontal axis indicate categories of the defect origin, and the vertical axis indicates a frequency of defect generation of a defect belonging to each category.

As described above, the defect image processing apparatus 11 can display the defect image 53, the layout image 52 of a layer which is likely to be a defect origin above or below the layer containing the defect and the layout image & defect image 54 which is formed by superimposing the layout image 52 on the defect image 53, on the same display screen 50. Therefore, the operator who conducts a defect analysis can easily estimate whether or not another layer has effects on the defect by observing the display screen 50. As a result, the analysis of the defect origin can be easily conducted.

Figure 6:
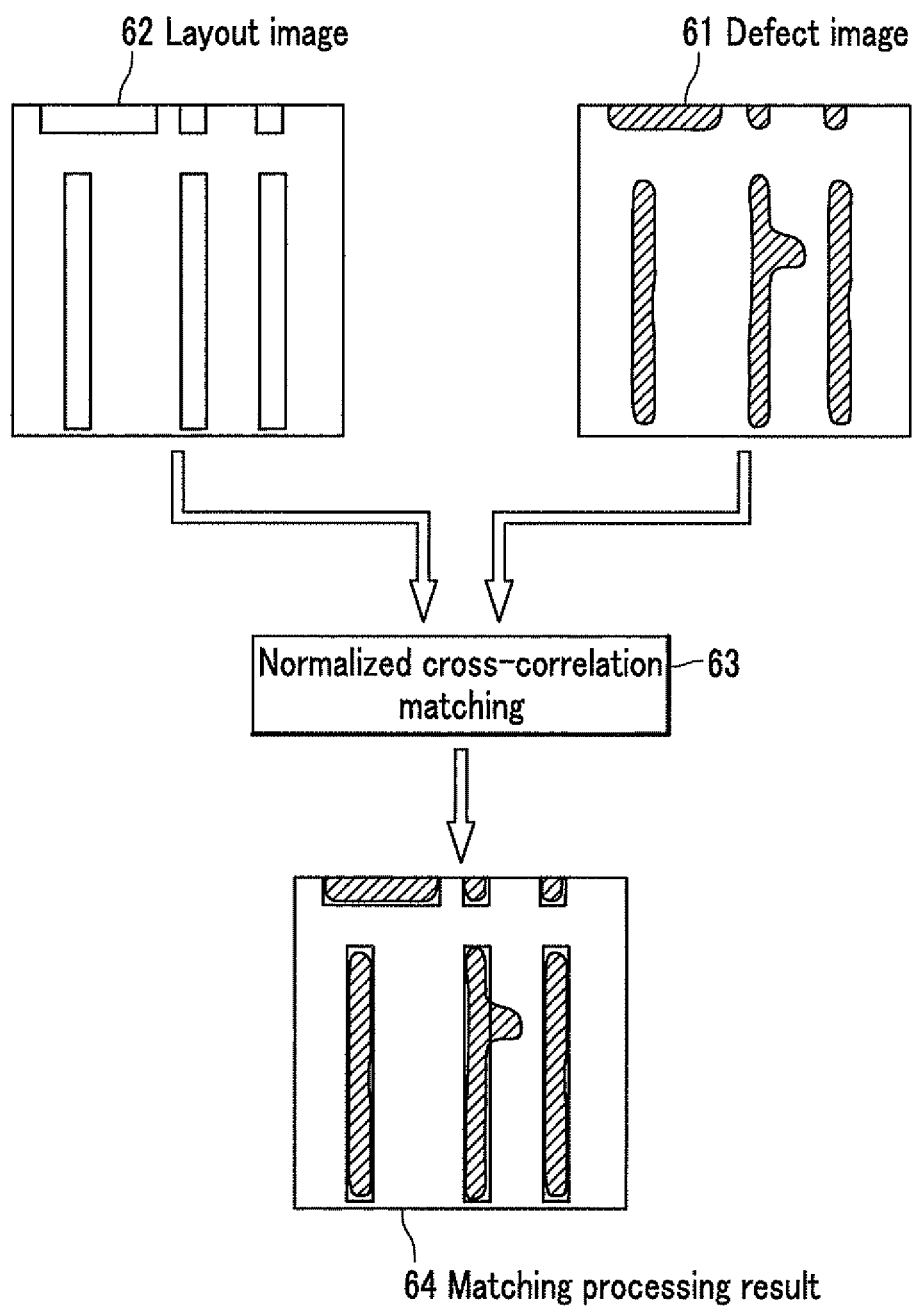
FIG. 6 is an illustration showing an outline of a matching processing in a defect image processing apparatus according to the embodiment of the present invention.

Next, an explanation will be given of a matching processing executed in the defect image processing apparatus 11 in detail by referring to FIG. 6 to FIG. 8. FIG. 6 is an illustration showing an outline of the matching processing in the defect image processing apparatus 11.

As described above, it is likely to be a gap in many cases between a defect image 61 acquired, for example, by the review device 5 and a layout image 62 generated from the layout data 23 due to a position detection error of, for example, the review device 5.

The matching processing unit 47 executes an automatic matching between the defect image 61 and the layout image 62, using a well-known normalized cross-correlation matching 63, and outputs a matching processing result 64. In this case, the matching may be failed in some case due to the foregoing position detection error. Therefore, a search area of the layout image 62 is set larger than the area of the defect image 61 in order to execute the matching processing with the defect image 61. Meanwhile, the search area can be set appropriately by operation of the operator.

Meanwhile, the number of layer of the layout image of a matching processing target in the matching processing unit 47 is basically one layer. However, for example, when a poly-Si layer is observed by the review device 5, a pattern of a device isolation layer below the poly-Si layer is also seen. Namely, the acquired poly-Si layer image (defect image 61) acquired by, for example, the review device 5 also includes an image of the device isolation layer. Therefore, in this case, an image which is formed by superimposing the layout image of the poly-Si layer on the layout image of the device isolation layer is used as the layout image of the matching processing target.

In addition, in the matching processing, if a ratio of area occupied by a defect portion to a whole area of the defect image 61 is small, a successful matching probability between an image other than the defect portion of the defect image 61 and the layout image 62 is large. On the other hand, if the ratio of area occupied by the defect portion to the whole area of the defect image 61 is large, the matching is likely to fail in many cases because the defect portion itself forms a barrier for the matching. Therefore, the successful matching probability is increased, using a matching method described below.

Meanwhile, the review device 5 (see FIG. 1) generally acquires a review image of some area at a low magnification, and, for example, the review image is compared with a reference image acquired in the same area of the neighboring die in order to detect existence or non-existence of a defect by the difference image. If the defect is detected, the review device 5 acquires a review image of the area containing the defect portion at a high magnification. In addition, when ADC is conducted, a reference image of high magnification is used in order to improve classification accuracy by the ADC.

As described above, four types of review images, which are a defect image of low magnification, a reference image of low magnification, a defect image of high magnification and a reference image of high magnification, are acquired by the review device 5. Next, an explanation will be given of the matching processing which uses an image of high magnification. Meanwhile, when there is no review image of high magnification, a review image of high magnification (defect image or reference image) may be prepared by cutting an area containing the defect portion from the review image of low magnification and magnifying the area.

Figure 7:
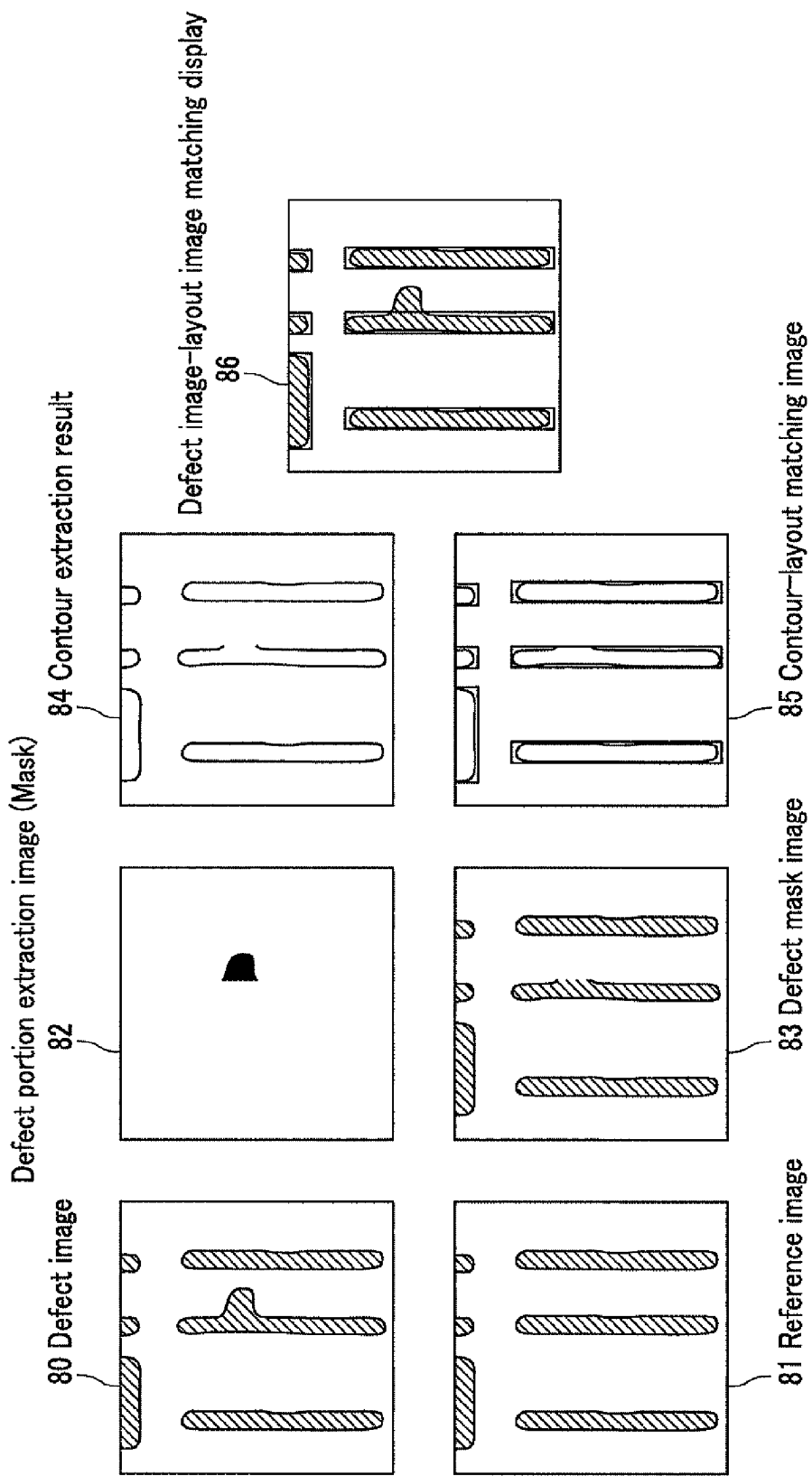
FIG. 7 is an illustration showing one example of a matching method when a reference image is available in a defect image processing apparatus according to the embodiment of the present invention.

FIG. 7 is an illustration showing one example of a matching processing method in the case that a reference image is acquired in the defect image processing apparatus 11.

The defect image processing apparatus 11 acquires a defect image 80 acquired by the review device 5, a reference image 81 and an image information file 20 for each image, from the defect data management apparatus 7.

The matching processing unit 47 acquires a defect portion extraction image 82 by acquiring a difference between the defect image 80 and the reference image 81. Next, the matching processing unit 47 prepares a defect mask image 83 that is generated by removing the defect portion extraction image 82 from the defect image 80, that is, an image that masks the defect portion extraction image 82 of the defect image 80. Furthermore, the matching processing unit 47 extracts a contour from the defect mask image 83 and acquires a contour extraction result 84.

Next, the matching processing unit 47 acquires a contour-layout matching image 85 according to the matching method shown in FIG. 6, and based on the result, the output processing unit 49 outputs a defect image-layout image matching display 86 which is formed by superimposing the defect image on the layout image to the output unit 34.

In addition, when a defect portion is large enough to occupy most of the whole defect image, the matching processing may be conducted by executing a processing similar to the processing described in FIG. 7, by using a defect image of low magnification and a reference image of low magnification, which are acquired by the review device 5.

Next, an explanation will be given of the case that the reference image 81 is not acquired. FIG. 8 is an illustration showing one example of a matching method in the case that the reference image 81 is not acquired in the defect image processing apparatus 11.

The image file 19 acquired by the defect inspection device 3 or the review device 5 is provide with the image information file 20 (see FIG. 1), and information of the center of gravity coordinate and defect size of a defect contained in the image file 19 is generally included in the image information file 20. Then, as shown in FIG. 8, if the defect portion is a rectangular area having a horizontal distance $X_D$ and a vertical distance $Y_D$ in the defect image 80 of high magnification, the matching processing unit 47 generates a rectangular area having a horizontal distance $X_M$ ($>X_D$) and a vertical distance $Y_M$ ($>Y_D$), and prepares a defect portion extraction image 91.

Hereinafter, as with the case of FIG. 7, the matching processing unit 47 prepares a defect mask image 92 that is generated by removing the defect portion extraction image 91 from the defect image 80, that is, an image that masks the defect portion extraction image 91 of the defect image 80. Furthermore, the matching processing unit 47 extracts a contour from the defect mask image 92 and acquires a contour extraction result 93.

In addition, the matching processing unit 47 acquires a contour-layout matching image 94 according to the matching method shown in FIG. 6, and based on the result, the output processing unit 49 outputs a defect image-layout image matching display 86 which is formed by superimposing the defect image on the layout image, to the output unit 34.

Meanwhile, here, the defect portion extraction image 91 to be used as a mask was assumed to be a rectangular shape, however, the defect portion extraction image 91 may be a circular shape or an ellipsoidal shape, and is not limited to the rectangular shape. In addition, when a defect portion is large enough to occupy most of the whole defect image, the matching processing may be conducted by executing a processing similar to the processing described in FIG. 8, by using a defect image of low magnification acquired by the review device 5.

Figure 8:
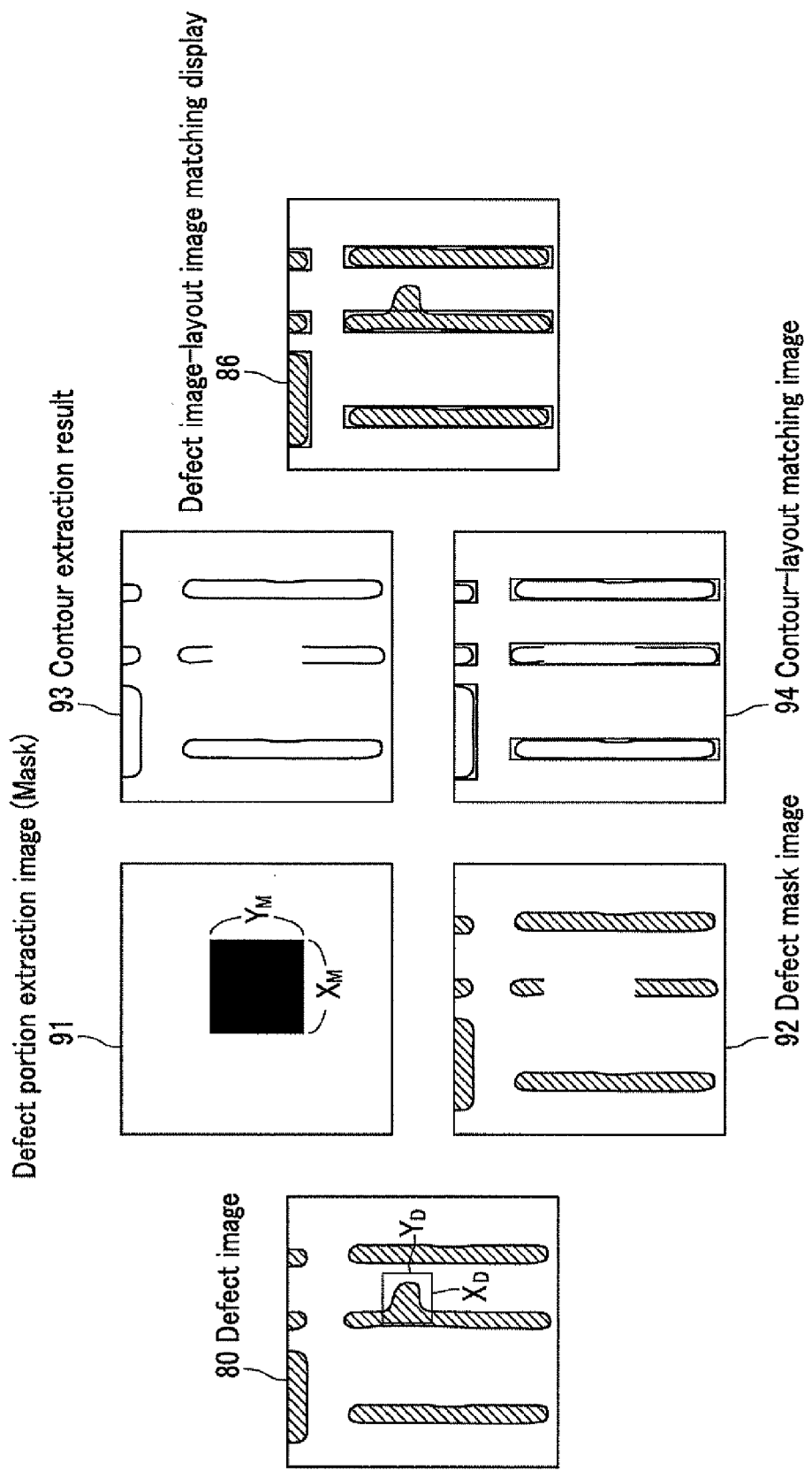
FIG. 8 is an illustration showing one example of a matching method when a reference image is not available in a defect image processing apparatus according to the embodiment of the present invention.

According to the foregoing description, if the image matching method described by using FIG. 7 or FIG. 8 is used, even if the review image (defect image) includes a defect, a failure probability of the image matching with a layout image (no defect) corresponding to the area of the defect can be decreased.

Figure 9:
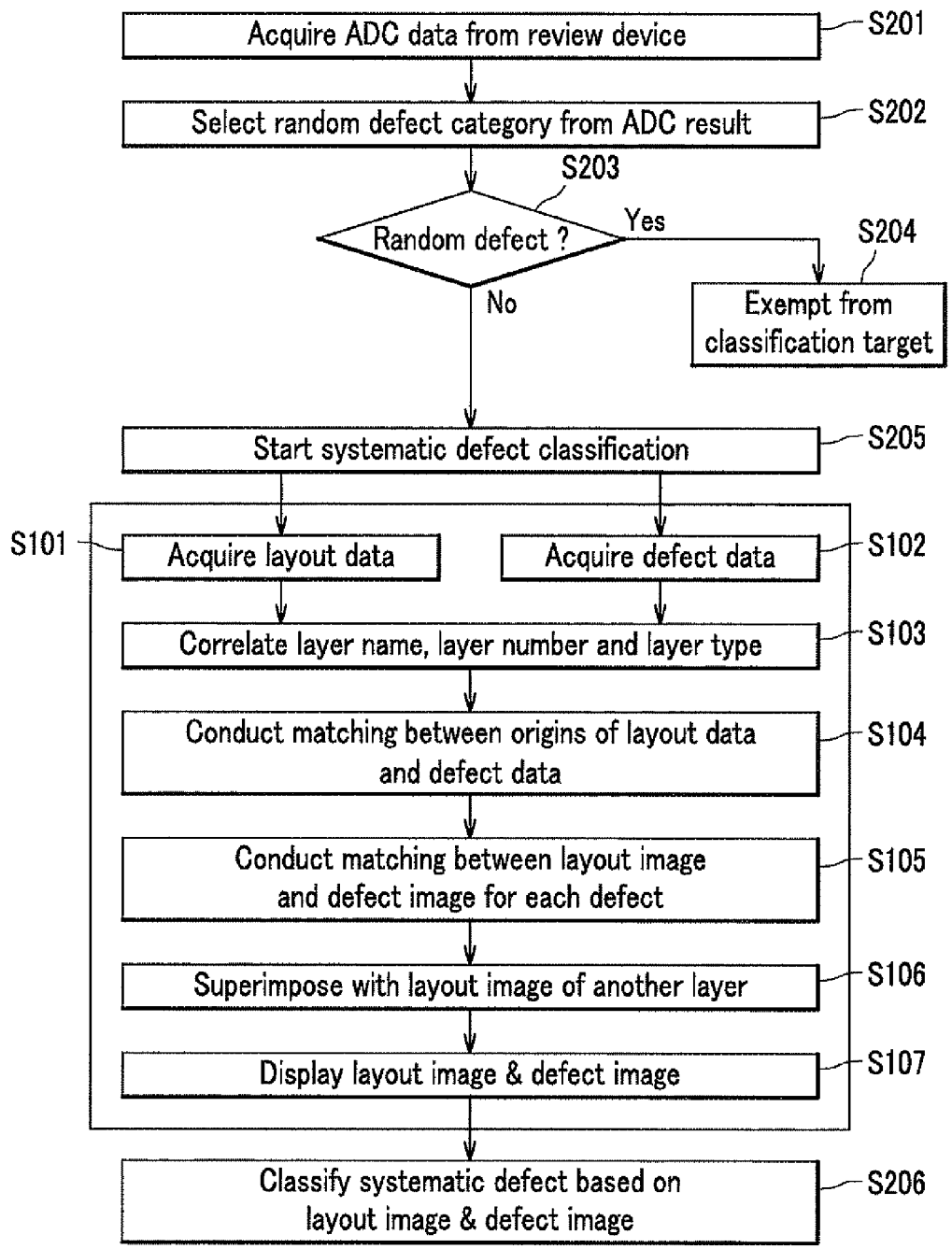
FIG. 9 is an illustration showing one example of a procedure of a systematic defect classification using a defect image processing apparatus according to the embodiment of the present invention.

FIG. 9 is an illustration showing one example of a procedure of a systematic defect classification using the defect image processing apparatus 11.

The data acquisition unit 41 of the defect image processing apparatus 11 first acquires the defect date 17 from the defect data management apparatus 7, and acquires ADC classification data acquired by the review device 5 (step S201). Then, the defect determination unit 45 selects a category of a random defect from the ADC classification data (step S202), and determines whether or not each defect contained in the defect data 17 is a random defect (step S203).

Next, as a result of the determination, if the defect is determined to be a random defect (step S203: Yes), the defect is exempted from a systematic defect classification (step S204). In addition, if the defect is determined not to be a random defect (step S203: No), the systematic defect classification is started by determining that the defect is a systematic defect (step S205).

After that, the defect image processing apparatus 11 executes processing of steps S101 to S107 which is identical to the processing described in FIG. 4, and displays the display screen 50 shown in FIG. 5. Then, the operator who conducts a defect analysis classifies the systematic defect based on the layout image & defect image 54 shown on the display screen 50 (step S206).

Meanwhile, in this case, the operator determines whether the defect is a systematic defect or not based on, for example, a relative positional relationship between a defect part (defect portion) of the defect displayed in the layout image & defect image 54 and a layout image of the upper or lower layer, that is, another layer of the layer containing the defect, and further classifies the systematic defect in detail.

If a method for determining whether or not a defect is a systematic defect and a method for further classifying the defect in detail are set up in advance as a rule with which a computer can determine the defect using the methods, the defect image processing apparatus 11 can automatically execute the defect classification. In this case, the defect image processing apparatus 11 may be called as a semiconductor defect classifying apparatus.

Meanwhile, as a rule for determining a defect to be a systematic defect and classifying the defect, for example, the rule may be defined in advance in such a manner that, for example, if a defect portion of the defect is located in the center portion of a significant area (the significant area means, for example, an impurity doping area, gate and wiring areas, and a contact hole area) of another layer, the defect corresponds to the first systematic defect, if the defect portion is located in a periphery portion of the significant area, the defect corresponds to the second systematic defect, and if the defect portion is located outside the significant area, the defect does not correspond to the systematic defect.

As described above, in the defect image processing apparatus 11 or in a semiconductor defect classifying apparatus using the defect image processing apparatus 11, a defect determined as a random defect based on ADC results is removed in advance. Subsequently, with respect to a defect other than the random defect, the defect image 53 of the defect is matched with the layout image 52 of a layer containing the defect and the upper layer or the lower layer, that is, another layer of the layer containing the defect, and the layout image and defect image 54 that is generated by superimposing the defect image 53 on the layout image 52 is displayed on a display screen. Therefore, the operator can easily determine whether or not a defect is a systematic defect and can easily classify the defect, and as a result, the work efficiency can be improved.

As described above, according to the defect image processing apparatus 11 embodying the present invention, or the semiconductor defect classifying apparatus using the defect image processing apparatus 11, a failure probability is reduced even if the layout image is matched with the defect image of high magnification, and as a result, efficiency of the image matching is improved. In addition, not only the layout image of a layer identical to the layer of the defect image, but also a superimposed image which is formed by superimposing a layout image of another layer on the layout image of the layer identical to the layer of the defect image is also displayed. Therefore, these images can be utilized for classifying a systematic defect which is generated affected and caused by the design of another layer and the fabrication process, and as a result, efficiency of analysis of the defect origin can be improved.

DESCRIPTION OF REFERENCE

1 Semiconductor inspection system
3 Defect inspection device
5 Review device
7 Defect data management apparatus
8 Clean room
9 Design database server
10 Network
11 Defect image processing apparatus
17 Defect data
18 Defect data file
19 Image file
20 Image information file
23 Layout data
30 Communication unit
31 Control unit
32 Storage unit
33 Input unit
34 Output unit
41 Data acquisition unit
43 Data conversion unit
45 Defect determination unit
47 Matching processing unit
49 Output processing unit
50 Display screen
51 Layer correlation display
52 Layout image
53 Defect image
54 Layout image & defect image
55 Wafer map display
56 Die map display
57 Defect category display
58 Shifting button

What is claimed is:

1. A defect image processing apparatus, comprising:
a matching processing unit that executes an image matching between a defect image, which is acquired by a defect inspection device or a defect review device of a semiconductor device, of a portion containing a defect of the semiconductor device and a layout image, which is generated from a layout data of the semiconductor device, of an area corresponding to an area of the defect image in a layer identical to a layer containing the defect; and
an output processing unit that displays a superimposed image which is formed by superimposing the defect image on the layout image, on a display unit, the defect image being matched with the layout image by the matching processing unit,
wherein when the image matching between the defect image and the layout image is executed, the matching processing unit removes or masks an image of an area of a defect portion from the defect image and executes the image matching between the layout image and a remaining image that is formed by removing or masking the image of the area of the defect portion from the defect image.

2. The defect image processing apparatus according to claim 1, wherein the area of the defect portion is an area acquired as a difference image between the defect image acquired by the defect inspection device or the defect review device and a review image of another portion having a structure identical to a structure of the defect image of the semiconductor device.

3. The defect image processing apparatus according to claim 1, wherein the area of the defect portion is defined by a position and size of the defect acquired by the defect inspection device or the defect review device for the defect included in the defect image.

4. The defect image processing apparatus according to claim 1, wherein when the image matching between the defect image and the layout image is executed, the matching processing unit determines a magnification of the layout image so as to match with a magnification of the defect image which is acquired by the defect inspection device or the defect review device and sent from the defect inspection device or the defect review device.

5. The defect image processing apparatus according to claim 1, wherein when the superimposed image is displayed, the output processing unit further superimposes the layout image of an area corresponding to the area of the defect image in a layer different from the layer containing the defect, on the superimposed image.

6. The defect image processing apparatus according to claim 1,
wherein the output processing unit concurrently displays the defect image, the layout image and the superimposed image on the same screen of the display unit.

7. A defect image processing method executed by a computer, comprising:
executing an image matching between a defect image, which is acquired by a defect inspection device or a defect review device of a semiconductor device, of a portion containing a defect of the semiconductor device and a layout image, which is generated from a layout data of the semiconductor device, of an area corresponding to an area of the defect image in a layer identical to a layer containing the defect; and
displaying a superimposed image which is formed by superimposing the defect image on the layout image, on a display unit, the defect image being matched with the layout image by the matching processing unit,
wherein when the image matching between the defect image and the layout image is executed, the computer executes:
removing or masking an image of an area of a defect portion from the defect image; and
executing the image matching between the layout image and a remaining image that is formed by removing or masking the image of the area of the defect portion from the defect image.

8. The defect image processing method according to claim 7, wherein the area of the defect portion is an area acquired as a difference image between the defect image acquired by the defect inspection device or the defect review device and a review image of another portion having a structure identical to a structure of the defect image of the semiconductor device.

9. The defect image processing method according to claim 7, wherein the area of the defect portion is defined by a position and size of the defect acquired by the defect inspection device or the defect review device for the defect included in the defect image.

10. A semiconductor defect classifying apparatus, comprising:
a matching processing unit that executes an image matching between a defect image, which is acquired by a defect inspection device or a defect review device of a semiconductor device, of a portion containing a defect of the semiconductor device and a layout image, which is generated from a layout data of the semiconductor device, of an area corresponding to an area of the defect image in a layer identical to a layer containing the defect;
an output processing unit that displays a superimposed image which is formed by superimposing the defect image on the layout image, on a display unit, the defect image being matched with the layout image by the matching processing unit; and
a defect determination unit that determines whether or not the defect is a systematic defect having a layout dependency,
wherein when the image matching between the defect image and the layout image is executed, the matching processing unit removes or masks an image of an area of a defect portion from the defect image and executes the image matching between the layout image and a remaining image that is formed by removing or masking the image of the area of the defect portion from the defect image; and
wherein the defect determination unit determines whether or not the defect is the systematic defect based on a relationship between a position of the defect and the layout image acquired from the superimposed image.

11. The semiconductor defect classifying apparatus according to claim 10, wherein when a classification data is attached to defects of the semiconductor device acquired by the defect inspection device or the defect review device, the defect determination unit removes a defect classified in a random defect from a category of the systematic defect.

12. A semiconductor defect classifying method of a semiconductor defect classifying apparatus comprising:
a matching processing unit that executes an image matching between a defect image, which is acquired by a defect inspection device or a defect review device of a semiconductor device, of a portion containing a defect of the semiconductor device and a layout image, which is generated from a layout data of the semiconductor device, of an area corresponding to an area of the defect image in a layer identical to a layer containing the defect;
an output processing unit that displays a superimposed image which is formed by superimposing the defect image on the layout image, on a display unit, the defect image being matched with the layout image by the matching processing unit; and
a defect determination unit that determines whether or not the defect is a systematic defect having a layout dependency,
wherein when the image matching between the defect image and the layout image is executed, the matching processing unit:
removing or masking an image of an area of a defect portion from the defect image; and
executing the image matching between the layout image and a remaining image that is formed by removing or masking the image of the area of the defect portion from the defect image; and wherein the defect determination unit:
determining whether or not the defect is the systematic defect based on a relationship between a position of the defect and the layout image acquired from the superimposed image.

13. The semiconductor defect classifying method according to claim 12, wherein when a classification data is attached to defects of the semiconductor device acquired by the defect inspection device or the defect review device, the defect determination unit:
removing a defect classified in a random defect from a category of the systematic defect.

* * * * *